United States Patent [19]
Gonzalez et al.

[11] Patent Number: 5,831,095
[45] Date of Patent: Nov. 3, 1998

[54] SYNTHESIS OF 5-AMINOCARBONYL-5H-DIBENZO[A,D]CYCLOHEPTEN-5,10-IMINE

[75] Inventors: Javier Gonzalez, San Diego, Calif.; F. Ivy Carroll, Durham, N.C.

[73] Assignee: Research Triangle Institute, Research Triangle Park, N.C.

[21] Appl. No.: 715,480

[22] Filed: Sep. 18, 1996

Related U.S. Application Data

[60] Provisional application No. 60/004,315, Sep. 26, 1995.
[51] Int. Cl.$^6$ .................................................. C07D 221/18
[52] U.S. Cl. .................................................. 546/72
[58] Field of Search ................................. 546/72

[56] References Cited

U.S. PATENT DOCUMENTS

| | | | |
|---|---|---|---|
| 4,232,158 | 11/1980 | Shepard et al. | 546/72 |
| 5,196,415 | 3/1993 | Monn et al. | 514/210 |
| 5,239,039 | 8/1993 | Markle | 528/44 |

FOREIGN PATENT DOCUMENTS 04363657  12/1992  Japan .

OTHER PUBLICATIONS

March, J., Advanced Organic Chemistry, Wiley & Sons, pp. 811, 812, and 966, Jun. 1993.
Dygos, J.H., J. Heterocycle Chem. 1976, 13, pp. 1355–1357.
Hutchins, R.O. et al, J. Org. Chem. 1978, 43(11), pp. 2259–2267.
Snyder, H.R. et al, J. Am. Chem. Soc. 1954, 767, pp. 3039–3040.
Gonzalez, J. et al, Tetrahedron Letters, 1996, 37(48), pp. 8655–8658.

*Primary Examiner*—Bernard Dentz
*Assistant Examiner*—Garth M. Dahlen
*Attorney, Agent, or Firm*—Oblon, Spivak, McClelland, Maier & Neustadt, P.C.

[57] ABSTRACT

A powerful new anti-convulsant and anti-ischemic pharmaceutical, 5-aminocarbonyl-5H-dibenzo[a,d]cycloheptene-5,10-imine is prepared according to a novel synthesis which converts the starting material, commercially available dibenzosubernone to ADCI without the use of chromatographic purification, hazardous reagents or extreme conditions. The starting material is converted to the corresponding imine through ammonia exposure, and directly converted with acetone cyanohydrin in the presence of sodium cyanide to a 5-amino, 5-cyanocycloheptene intermediate. The intermediate is cyclized using bromine, followed by a reduction of the bromine-carbon bond using sodium cyanoborohydride. The target compound is obtained through selective hydrolysis. An overall yield of 46 percent or better is obtained.

8 Claims, No Drawings

SYNTHESIS OF 5-AMINOCARBONYL-5H-DIBENZO[A,D] CYCLOHEPTEN-5,10-IMINE

This application is a continuation of provisional application No. 60/004,315, Sep. 26, 1995.

BACKGROUND OF THE INVENTION

1. Field of the Invention

5-Aminocarbonyl-5H-dibenzo[a,d]cyclohepten-5,10-imine (ADCI) is a promising new pharmaceutical currently undergoing clinical trials as an anticonvulsant. This application provides a new method for synthesizing this pharmaceutical safely, under higher yields than available in the prior art.

2. Background of the Prior Art

ADCI has been identified as pharmaceutical having a mechanism of action different from recognized anticonvulsants. This pharmaceutical is currently undergoing clinical trials for use as an anticonvulsant. ADCI also appears to offer potential as an anti-ischemic, particularly for treatment of conditions currently not treatable.

ADCI was first described by Monn et al., J. Med. Chem., 33, 1069–1076 (1990), see also U.S. Pat. No. 5,196,415. The synthesis of the compounds set forth requires eight steps, and provides an overall yield of 33%. Additionally, the synthetic route provided involves several steps that may be problematical for preparative-scale work. Thus, the published synthesis requires two separate chromomatagraphic purifications, which are particularly expensive when done on a large scale. Further, one of the eight synthetic steps requires sec-butyllithium and ether, a combination which presents a severe fire hazard. Generally, use of diethyl ether in plant operations is avoided because of the fire hazard presented. The presence of sec-butyllithium, a pyrophoric reagent, compounds this risk. Further, the step of the synthetic scheme published using these reagents requires a temperature of −78° C., which is difficult to achieve and maintain in large-scale operations.

The clinical trials for ADCI appear to be going well, and acceptance of this powerful new pharmaceutical for one or more utilities may be recognized in the immediate future. A major impediment to its development, however, is the cumbersome, relatively low yield process, that requires special reagents, chromatographic separations, and low temperature reactions.

Accordingly, it remains a goal of those of skill in the art to provide a synthesis route for ADCI that provides a relatively rapid synthetic scheme, with an improved yield, and avoiding the problems that characterize the only known process for synthesis thereof, particular reagents, separations, and reaction conditions required.

SUMMARY OF THE INVENTION

The above objects, and others made more clear by the discussions set forth below, is achieved through five-step process, beginning with the commercially-available ketone dibenzosuberenone. Conversion of the starting material to the corresponding imine is achieved in sufficiently pure form to be used directly in the next synthetic step, although crystallization may be practiced. Conversion to the amino nitrile was followed by ready crystallization of this intermediate from the reaction mixture by treatment with acetone cyanohydrin in ethanol, using small amounts of NaCN.

The crystallized olefinic amino nitrile is oxidatively cyclized with bromine, followed by reduction of the benzylic carbon-halogen bond, to give the nitrile followed by removal of the polar aprotic solvent. Again, the intermediate obtained was sufficiently pure to be used directly in selective hydrolysis to give ADCI.

Overall yield, beginning with the starting material, may be higher than 46%, and the inventive process offers a relatively rapid synthesis scheme, starting from the commercially available ketone and going to completion relatively rapidly. Indeed, four out of five steps proceed to completion in less then about two hours. Because the intermediates are either pure enough to be used, in situ, for the next synthetic step, or crystalize easily and rapidly from the reaction mixture, complicated purifications are avoided, without the use of extreme reaction conditions.

DETAILED DESCRIPTION OF THE INVENTION

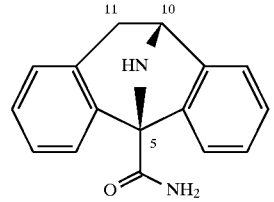

The synthesis of ADCI (1) (above) in five steps from dibenzosubernone is described in Scheme 1 (below). Conversion of the commercially-available ketone dibenzosubernone to the known imine 2 was effected using $TiCl_4$ and ammonia as described in Brenner et al., J. Het. Chem. 22, 805 (1985). Although compound 2 could be crystallized, it was sufficiently pure to be used directly in the next step. The α-aminonitrile 3 crystallized readily from the reaction mixture when 2 was treated with acetone cyanohydrin in ethanol using a catalytic amount (5 mole %) of NaCN. Aminonitrile 3 could also be obtained by treatment of 2 with TMSCI, KI, and NaCN in acetonitrile, but in this case the reaction was slower (~1 day), and required a basic aqueous workup.

Bromine-pronatal cyclization of the olefinic aminonitrile 3 was achieved using bromine in methylene chloride. This reaction, which is slightly exothermic, initially afforded 55–60% yield of the expected bromide 4 as a white solid. The material remaining in the mother liquors was found to be mainly a mixture of unreacted starting material and N-brominated 4. Thus, treatment of the mother liquors with additional bromine, followed by washing with aqueous sodium carbonate and sodium thiosulfate (which reduces the N-brominated product), afforded 4 in 88% isolated yield. Although the bromination described in the experimental section involved addition of bromine at −65° C. followed by warming to room temperature, this is not necessary. When bromine was added to a solution of 3 at 25° C. on a 0.02 mole scale, and the thiosulfate wash omitted, compound 4 and its N-bromo derivative were isolated upon fractional crystallization.

Reduction of the benzylic carbon-halogen bound in 4 was effected cleanly using sodium cyanoborohydride in N-methylpyrrolidinone (NMP) at 100° C. for 40 min. See, generally, Hatchins et al., J. Org. Chem. 43, 2259 (1978). The nitrile 5 was obtained following an aqueous workup to remove the polar aprotic solvent. Although it could be purified by recrystallization, 5 was obtained pure enough (<5% of non-volatile impurities by $^1H$ NMR) to be used in the next step. Use of DMPU at 80° C. also afforded 5 cleanly, but this solvent was difficult to remove from the product.

Selective hydrolysis of 5 to ADCI (1) was effected by heating in polyphosphoric acid. Selective hydrolysis using polyphosphoric acid is addressed, generally, in Snyder et al., J. Am. Chem. Sol. 76, 3039 (1954). Alternatively, exposure of the nitrile to 80% sulfuric acid at room temperature overnight also afforded ADCI in 69% yield.

1 h the mixture consisted of a thick slurry. To this was added water (10 mL), and stirred for another hour, then filtered. The filter cake was washed with 95% ethanol (4×25 mL) and dried, affording a white crystalline solid (17.21 g). The filtrate was concentrated under aspirator vacuum at a bath temperature of 45° C. to a volume of ~50 mL, and allowed

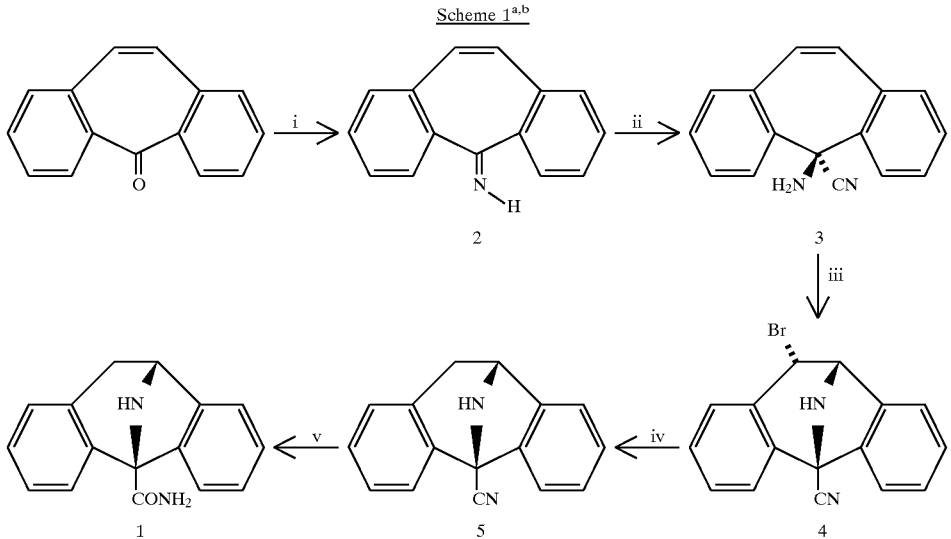

Scheme 1[a,b]

[a]Conditions:
i) TiCl$_4$, NH$_3$, Toluene, 25° C., 16 h (93%)
ii) acetone cyanohydrin, NaCN (cat), EtOH (88%)
iii) Br$_2$, CH$_2$Cl$_2$ 25° C., 1 h; workup with Na$_2$S$_2$O$_3$ (aq), repeat (88%)
iv) NaBH$_3$CN, NMP, 100° C., 40 min. (83%)
v) PPA, 100° C., 30 min (77%)
[b]Steps iii–v in this scheme involved aqueous workups with 10% Na$_2$CO$_3$.

EXPERIMENTAL SECTION

Dibenzosuberenone imine (2).

The following procedure is a modification of one reported by Brenner et al. The following was performed in a 1 L, 3-necked flask fitted with a thermometer, gas inlet tube, and mechanical stirrer: To a solution of dibenzosuberenone (20.62 g, 0.10 mol) in toluene (600 mL) at −5° C.±5° C. was added neat titanium tetrachloride (16.45 mL, 0.15 mol), under nitrogen, resulting in the formation of a black or very dark red curd-like suspension. Anhydrous ammonia was bubbled through the mixture at −5° C. at such a rate that very little gas escaped from the bubbler. The color gradually changed to yellow over the course of 45 min, and shortly thereafter the mixture became saturated with ammonia. The flow of gas was discontinued, the cooling bath removed, and the slurry stirred for 16 h at room temperature.

The slurry was filtered, the cake washed with toluene (100 mL), and the filter cake slurried in hot toluene (300 mL). This operation was repeated, and the combined filtrates evaporated, affording 19.19–20.36 g (93–99%) of material that was pure except for a small amount (2–5%) of unreacted ketone. This compound was obtained as a resin that was carried directly to the next step without purification.

5-Amino-5-cyano-5H-Dibenzo[a,d]cycloheptene (3)

To the crude imine (19.19 g containing ~0.088 mol of 2) was added acetone cyanohydrin (27.4 mL, 0.30 mol), 95% ethanol (100 mL), and sodium cyanide (0.25 g, 0.005 mol), and the mixture vigorously stirred, resulting in the formation of a solution. Crystals began to appear after 10 min, and after 1 h the mixture consisted of a thick slurry. To this was added water (10 mL), and stirred for another hour, then filtered. The filter cake was washed with 95% ethanol (4×25 mL) and dried, affording a white crystalline solid (17.21 g). The filtrate was concentrated under aspirator vacuum at a bath temperature of 45° C. to a volume of ~50 mL, and allowed to crystallize over the course of an hour at room temperature. The crystals were filtered, washed with ethanol (4×5 mL), and dried, affording another 1.80 g solid. The combined yield of product was 19.01 g (82% from dibenzosuberenone). An analytically-pure sample was prepared by recrystallization from ethyl acetate/petroleum ether; mp 128°–133° C. (dec, gas); R$_f$ 0.5 (1:4 ethyl acetate/petroleum ether+1% sat'd NH$_3$/CH$_3$OH); Anal Calc'd for C$_{16}$H$_{12}$N$_2$: C, 82.73; H, 5.21; N, 12.06; Found: C, 82.68; H, 5.25; N, 12.06.

11 α-Bromo-5-cyano-5H-Dibenzo[a,d]cyclohepten-5,10-imine (4)

To a suspension of the aminoalkene (3, 19.01 g, 0.0818 mol) in methylene chloride (100 mL) at −65° C.±5° C. was added bromine (4.4 mL, 0.085 mol) in methylene chloride (20 mL) over 5 min, and the mixture allowed to warm to room temperature over the course of 1 h. Following the addition of the bromine, the starting material dissolved, affording a red solution. Over several minutes the red color was discharged, resulting in the formation of a yellowish slurry. The reaction mixture was stirred with 10% aqueous Na$_2$CO$_3$ (50 mL), and 20% aqueous Na$_2$S$_2$O$_3$ (50 mL, to reduce N-brominated product). The mixture was transferred to a separatory funnel with the aid of methylene chloride (100 mL), and the organic phase separated and dried over Na$_2$SO$_4$. The volume was reduced by 50% by concentration in vacuo, and the resulting thick slurry diluted with cyclohexane (100 mL). The slurry was filtered, and the cake washed with 1:1 methylene chloride/cyclohexane (3×30 mL), and dried, affording 14.21 g product.

The filtrates were evaporated, affording 10.0 g solid. This was dissolved in methylene chloride (100 mL), and treated with bromine (2.2 mL 0.043 mol) in methylene chloride (20 mL) as described above, affording an additional 8.17 g product. Both batches, which are identical by TLC, amounted to 22.38 g (88%). mp 156°–157° C.; $R_f$ 0.6 (1:4 ethyl acetate/petroleum ether+1% sat'd $NH_3/CH_3OH$); $^1H$ NMR ($CDCl_3$) δ7.61–7.27 (m, 8H, ArH), 5,72 (d, J=5.5 Hz, 1H), 4.87 (d, J=5.5 Hz, 1H), 3.47 (br s, 1H, NH).

5-Cyano-5H-Dibenzo[a,d]cyclohepten-5,10-imine
(5)

To a mixture of the benzylic bromide (4, 22.38 g, 0.0719 mol) and sodium cyanoborohydride (18.08 g, 0.2877 mol) was added N-methylpyrrolidinone (80 mL), resulting in an increase in temperature to 55°–60° C. The frothing white suspension was stirred and heated to 100° C. The reaction was spontaneously exothermic upon reaching 80°–85° C. After 40 min at 100° C., the reaction mixture was diluted with water (400 mL), acidified with conc HCl (10 mL), basified with 30% NaOH (10 mL), and the resulting suspension extracted with methyl t-butyl ether (3×250 mL). The extracts were washed with water (3×200 mL), dried over $Na_2SO_4$, and evaporated, affording 16.23 g resin. By $^1H$ NMR, this consists of essentially pure title compound containing ~10 mole % solvent. It was used without further purification in the next step. $^1H$ NMR ($CDCl_3$) δ7.55–6.94 (m, 8H), 4.78 (d, J=5.5 Hz, 1H, H10), 3.37 (dd, J=17.2, 5.5 Hz, 1H, H11α), 2.99 (br s, 1H, NH), 2.68 (d, J–17.2 Hz, 1H, H11β).

An analytically pure sample was obtained by crystallization from ethyl acetate/petroleum ether; mp 116°–118° C. The hydrochloride salt was prepared by treating a solution of the free base in acetone with ethereal hydrogen chloride; mp 236°–238° C. Anal Calc'd for $C_{16}H_{13}ClN_2$: C, 71.51; H, 4.88; N, 10.42. Found: C, 71.32; H, 4.94; N, 10.47.

5-Aminocarbonyl-5H-Dibenzo[a,d]cyclohepten-5,
10-imine (6)

To the crude nitrile (5, 16.23 g, containing ~0.06 moles of 5) was added polyphosphoric acid (100 mL), and the resulting viscous heterogeneous mixture stirred with a glass rod and heated at 110° C.±10° C. at an oil bath temperature of 130° C.±10° C. After 30 min, the syrupy mass was transferred, while hot, to a large beaker, and quenched with ice (~300 mL). This procedure may be practiced with mechanical stirring, or in the alternative, use of a less viscous reagent such as 80% sulfuric acid. The solution was carefully basified with 30% NaOH, resulting in the precipitation of a dark resin. This mixture was vigorously stirred with ethyl acetate (200 mL), resulting in the formation of a beige suspension. The mixture was filtered, and the cake washed with water (2×30 mL) and ethyl acetate (2×30 mL), affording 12 g of crude ADCI. The ethyl acetate phase was separated from the filtrate and concentrated, affording another 2 g of product. The combined batches of solid were dissolved in 1M HCl (150 mL), treated with decolonizing charcoal, filtered, and basified, resulting in a white slurry. The solid was filtered, washed with water (4×50 mL, methanol (1×30 mL), ether (1×30 mL), and dried, affording the title product as a white solid (11.50 g, 64% overall from bromide 6); mp 238°–241° C. (uncorr), lit mp 235°–236° C. Monn et al., supra. The proton NMR of this material matched that reported by Rice et al. Thus, ADCI was obtained in 5 steps and in 46% overall yield from dibenzosuberenone.

The above invention has been described both generically, and by specific exemplification. Examples are not limiting, save where indicated, and alternatives will occur to those of ordinary skill in the art without the exercise of inventive activity. In particular, specific reagents, conditions and recoveries can be altered, without moving beyond the scope of the invention, save as delimited by the recitation of the claims set forth below.

What is claimed is;:

1. A method for synthesizing 5-aminocarbonyl-5H-dibenzo[a,d]cycloheptene-5,10-imine (ADCI) comprising:

converting dibenzosubernone to a corresponding imine in the presence of ammonia to produce intermediate A, reacting intermediate A with a cyanide-bearing reagent to produce a 5-amino, 5-cyano-cycloheptene intermediate B, oxidatively cyclizing intermediate B by bromination thereof to obtain an 11-α-bromo, 5-cyano-cycloheptene intermediate C, reducing a benzylic carbon-halogen bond of intermediate C in the presence of sodium cyanoborohydride to obtain intermediate D, and selectively hydrolyzing intermediate D to produce ADCI.

2. The process of claim 1, wherein said step of reacting intermediate A with a cyanide-bearing reagent comprises reacting intermediate A with acetone cyanohydrin in ethanol, in the presence of a catalytic amount of NaCN.

3. The method of claim 1, wherein said step of reacting intermediate A with a cyanide-bearing reagent comprises reacting intermediate A with TMSCI, KI and NaCN in acetonitrile.

4. The method of claim 1, wherein said bromination of intermediate B is performed in methylene chloride, and wherein a reaction mixture formed thereby is washed with aqueous sodium carbonate and sodium thiosulfate.

5. The method of claim 1, wherein the reduction of a benzylic carbon-halogen bond of intermediate C is effected in N-methylpyrrolidinone.

6. The method of claim 1, wherein said selective hydrolysis is achieved by heating intermediate D in polyphosphoric acid.

7. The method of claim 1, wherein said selective hydrolysis of intermediate D is achieved by combining said intermediate with 80 percent sulfuric acid at room temperature for a period of at least six hours.

8. The method of synthesizing ADCI, comprising the following reaction scheme:

Scheme 1

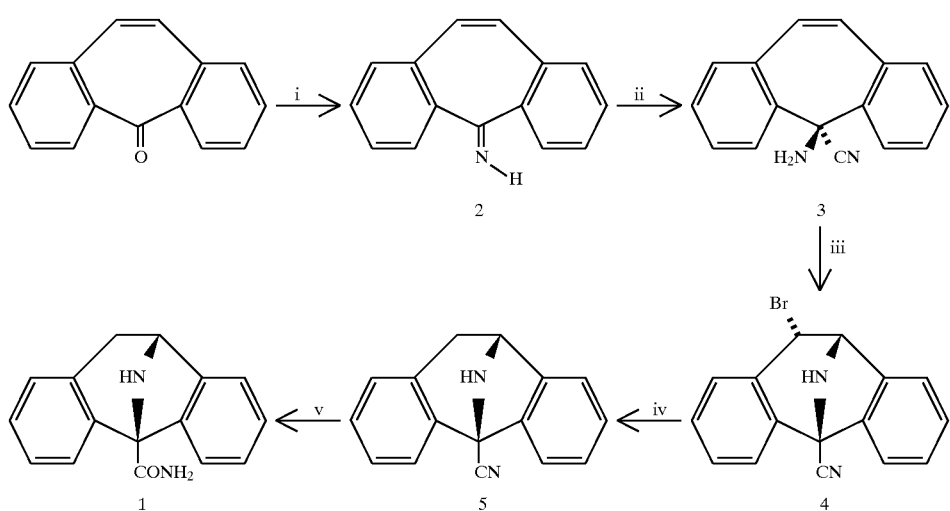

a) i) converting dibenzosubernone to 2 in the presence of TiCl$_4$ and NH$_3$, in Toluene, at 25° C., for 16 h, resulting in yield;
  ii) converting 2 to 3 in acetone in the presence of cyanohydrin, NaCN (cat) and EtOH;
  iii) converting 3 to 4 in CH$_2$Cl$_2$ in the presence of Br$_2$, at 25° C., for 1 h; followed by workup with Na$_2$S$_2$O$_3$ (aq), and repeat resulting in yield;
  iv) converting 4 to 5 in the presence of NaBH$_3$CN, NMP, at 100° C., for 40 min resulting in yield; and
  v) converting 5 to 1 in the presence of PPA, at 100° C., for 30 min resulting in yield; and
b) wherein Steps iii–v in this scheme involve aqueous workups with 10% Na$_2$CO$_3$.

* * * * *